(12) United States Patent
Marshall et al.

(10) Patent No.: US 8,673,857 B2
(45) Date of Patent: Mar. 18, 2014

(54) LONG TERM POTENTIATION WITH CYCLIC-GLUR6 ANALOGS

(75) Inventors: John Marshall, Barrington, RI (US); Andrew Mallon, Lincoln, RI (US)

(73) Assignee: Brown University, Providence, RI (US)

( * ) Notice: Subject to any disclaimer, the term of this patent is extended or adjusted under 35 U.S.C. 154(b) by 48 days.

(21) Appl. No.: 13/389,047

(22) PCT Filed: Aug. 27, 2010

(86) PCT No.: PCT/US2010/046891
§ 371 (c)(1),
(2), (4) Date: Feb. 28, 2012

(87) PCT Pub. No.: WO2011/025906
PCT Pub. Date: Mar. 3, 2011

(65) Prior Publication Data
US 2012/0149646 A1      Jun. 14, 2012

Related U.S. Application Data

(60) Provisional application No. 61/237,341, filed on Aug. 27, 2009.

(51) Int. Cl.
*A61K 38/00* (2006.01)
*A61K 38/10* (2006.01)

(52) U.S. Cl.
USPC .......................... 514/17.8; 514/17.7; 514/21.5

(58) Field of Classification Search
None
See application file for complete search history.

(56) References Cited

U.S. PATENT DOCUMENTS

| | | |
|---|---|---|
| 7,510,824 B2 | 3/2009 | Tymianski |
| 2002/0129385 A1 | 9/2002 | Mansuy et al. |
| 2003/0219378 A1 | 11/2003 | Piwnica-Worms |
| 2005/0222093 A1 | 10/2005 | Pearlman et al. |
| 2005/0281816 A1 | 12/2005 | Lamping et al. |

OTHER PUBLICATIONS

Migaud et al 1998 "Enhanced long-term potentiation and impaired learning in mice with mutant postsynaptic density-95 protein" Nature 396:433-439.*
Chen et al 2001 "molecular transporters for peptides: delivery of a cardioprotective ePKC agonist peptide into cells and intact ischemic heart using a transport system, R7" Chemistry and Biology 8/12:1123-1129.*
Niethammer et al 1998 "CRIPT, a novel postsynaptic protein that binds to the third PDZ domain of PSD-95/SAP90" Neuron 20:693-707.*
Cao et al 2013 "Impairment of TrkB-PSD95 signaling in Angelman syndrome" PLOS biology 11(2):1-16.*
2010 "Chapter 15: Delerium, Dementia, Amnestic, and other cognitive disorders" BVT publishing. First page. Accessed from http://www.bvtpublishing.com/files/BV21Chapter15.pdf.*
Piserchio et al., "Targeting Specific PDZ Domains of PSD-95: Structural Basis for Enhanced Affinity and Enzymatic Stability of a Cyclic Peptide", Chemistry & Biology, 2004, vol. 11, pp. 469-473.

(Continued)

*Primary Examiner* — Jeffrey Stucker
*Assistant Examiner* — Adam M Weidner
(74) *Attorney, Agent, or Firm* — Novak Druce Connolly Bove + Quigg LLP

(57) ABSTRACT

This invention discloses CN2097-like compositions that facilitate the induction of long-term potentiation (LTP). In one embodiment the method comprises inducing long-term potentiation in a subject by the method of administering a therapeutically effective dose of a CN2097-like compound.

6 Claims, 10 Drawing Sheets

(56) References Cited

OTHER PUBLICATIONS

PCT/US2010/046891 International Search Report dated Oct. 7, 2010.
Jiang, Y.-h. et al. Mutation of the Angelman Ubiquitin Ligase in Mice Causes Increased Cytoplasmic p53 and Deficits of Contextual Learning and Long-Term Potentiation. Neuron 21, 799-811 (1998).
Weeber, E.J. et al. Derangements of Hippocampal Calcium/Calmodulin-Dependent Protein Kinase II in a Mouse Model for Angelman Mental Retardation Syndrome. J. Neurosci. 23, 2634-2644 (2003).
van Woerden, G.M. et al. Rescue of neurological deficits in a mouse model for Angelman syndrome by reduction of [alpha]CaMKII inhibitory phosphorylation. Nat Neurosci 10, 280-282 (2007).
Yi, J.J. & Ehlers, M.D. Emerging Roles for Ubiquitin and Protein Degradation in Neuronal Function. Pharmacol Rev 59, 14-39 (2007).
Yi, J.J. & Ehlers, M.D. Ubiquitin and Protein Turnover in Synapse Function. Neuron 47, 629-632 (2005).
Elgersma, Y. et al. Inhibitory Autophosphorylation of CaMKII Controls PSD Association, Plasticity, and Learning. 36, 493-505 (2002).
Elgersma, Y., Sweatt, J.D. & Giese, K.P. Mouse Genetic Approaches to Investigating Calcium/Calmodulin-Dependent Protein Kinase II Function in Plasticity and Cognition. J. Neurosci. 24, 8410-8415 (2004).
Walz NC, B.G. Sensory processing patterns in persons with Angelman syndrome. Am J Occup Ther. 60, 472-9 (2006).
Williams, C. A. et al. Angelman syndrome 2005: Updated consensus for diagnostic criteria. American Journal of Medical Genetics Part A 140A, 413-418 (2006).
Oh-Nishi, A., Saji, M., Satoh, S.Z., Ogata, M. & Suzuki, N. Late phase of long-term potentiation induced by co-application of N-methyl-d-aspartic acid and the antagonist of NR2B-containing N-methyl-d-aspartic acid receptors in rat hippocampus. Neuroscience 159, 127-135 (2009).
Yashiro, K. et al. Ube3a is required for experience-dependent maturation of the neocortex. Nat Neurosci advanced online publication(2009).
Liu, L. et al. Role of NMDA receptor subtypes in governing the direction of hippocampal synaptic plasticity. Science 304, 1021-4 (2004).
Mallon, A.P., Auberson, Y.P. & Stone, T.W. Selective subunit antagonists suggest an inhibitory relationship between NR2B and NR2A-subunit containing N-methyl-D: -aspartate receptors in hippocampal slices. Exp Brain Res 162, 374-83 (2005).
Massey, P.V. et al. Differential Roles of NR2A and NR2B-Containing NMDA Receptors in Cortical Long-Term Potentiation and Long-Term Depression. J. Neurosci. 24, 7821-7828 (2004).
Morris, R. Developments of a water-maze procedure for studying spatial learning in the rat. Journal of Neuroscience Methods 11, 47-60 (1984).
Bienenstock, E.L., Cooper, L.N. & Munro, P.W. Theory for the development of neuron selectivity: orientation specificity and binocular interaction in visual cortex. J. Neurosci. 2, 32-48 (1982).
Giese, K.P., Fedorov, N. B., Filipkowski, R.K. & Silva, A.J. Autophosphorylation at Thr286 of the Alpha} Calcium-Calmodulin Kinase II in LTP and Learning. Science 279, 870-873 (1998).
Shen, K. & Meyer, T. Dynamic Control of CaMKII Translocation and Localization in Hippocampal Neurons by NMDA Receptor Stimulation. Science 284, 162-167 (1999).
Hardingham, G.E., Fukunaga, Y. & Bading, H. Extrasynaptic NMDARs oppose synaptic NMDARs by triggering CREB shut-off and cell death pathways. Nat Neurosci 5, 405-14 (2002).
Quinlan, E.M., Olstein, D.H. & Bear, M.F. Bidirectional, experience-dependent regulation of N-methyl-d-aspartate receptor subunit composition in the rat visual cortex during postnatal development. Proceedings of the National Academy of Sciences of the United States of America 96, 12876-12880 (1999).
Salinas, G.D., L.A.C. Blair, L.A. Needleman, J.D. Gonzales, Y. Chen, M. Li, J.D. Singer and J. Marshall. Actinfilin is a Cul3 substrate adaptor, linking GluR6 kainate receptor subunits to the ubiquitin-proteasome pathway. J. Biol. Chem. 281(52):40164-73, (2006).
Gao, L., L.A.C. Blair, G.D. Salinas, L.A. Needleman and J. Marshall. (2006). IGF 1-modulation of CaV1.3 calcium channels depends on $Ca+2$ release from IP3-senstitive stores and CaMKII-phosphorylation of the alpha1 subunit EF hand. J.Neurosci. 26, 6259-68
Gao, L., L.A.C. Blair and J. Marshall. (2006). CaMKII-independent effects of KN93 and its inactive analog KN92: reversible inhibition of L-type calcium channels. Biochem.Biophys.Res.Comm. 354, 1606-10.
Wang X, Tang X, Li M, Marshall J. Mao Z. (2005) Regulation of neuroprotective activity of myocyte-enhancer factor 2 by cAMP-protein kinase A signaling pathway in neuronal survival. J. Biol. Chem 280, 16705-13.
Ren, Z., Riley, N., Needleman, L., Sanders JM, Swanson GT, Marshall J. (2003) Cell surface expression of GluR5 kainate receptors is regulated by an endoplasmic reticulum retention. J. Biol. Chem. 26;278(52):52700-9.
Marshall J, Dolan BM, Garcia EP, Sathe S, Tang X, Mao Z, Blair L.A.C. (2003) Calcium channel and NMDA receptor activity differentially regulate nuclear C/EBP levels to control neuronal survival. Neuron 39: 625-629.
Ren Z, Riley NJ, Garcia EP, Sanders JM, Swanson GT, Marshall J. (2003) A Trafficking Checkpoint Controls Kainate Receptor Heterodimerization. J. Neuroscience 23, 6608-16.
Gong, X., Tang, X., Wiedmann, M., Wang, X., Peng, J., Zheng, D., Blair, L.A.C., Marshall, J., and Mao, Z (2003) Cdk-5-mediated inhibition of the protective effects of transcription factor MEF2 in neurotoxicity-induced apoptosis. Neuron 38:33-46.
Bowie, D., Garcia, E.P., Marshall, J., Traynelis, S.F. and Lange, G. David (2003) Allosteric Regulation and Spatial Distribution of Kainate Receptors Bound to Ancillary Proteins. J Physiol. 547:373-85
Piserchio, A., Pellegrini, M., Mehta, S., Blackman, S.M., Garcia, E.P., Marshall, J., and Mierke, D.F (2002) Structural Characterization of the Intermolecular Interaction of SAP90 with the GluR6-subunit of Kainate Receptors J. Biol. Chem. 277: 6967-6973.
Mehta, S., Wu, H., Garner, C.C., and Marshall, J (2001) Intramolecular interactions regulate SAP97 binding to kainate receptors. J. Biol. Chem. 276: 16092-16099.
Savinainen, A., Garcia, E.P., Dorow, D., Marshall, J., and Liu, Y-F (2001) Kainate Receptor Activation Induces Mixed Lineage Kinase-mediated Cellular Signaling Cascades via Post-synaptic Density Protein 95 J. Biol. Chem. 2001 276: 11382-11386.
Fukushima T., Shingai. R., and Marshall, J (2001) Calcium inhibits Willardiine-induced responses in kainate receptor GluR6(Q) and GluR6(Q)/KA-2 Neuroreport 12 163-167.
Liu, Y-F., Sudol, M., Marshall, J (2000) Assignment of molecular mechanisms of neuronal death underlying Huntington's disease. J. Biol. Chem. 275, 19035-19040.
Bence. K.K., Blair, L.A.C., and J. Marshall. (2000) Potentiation of neuronal L calcium channels by IGF-1 requires phosphorylation of the subunit on a specific tyrosine residue. Neuron 27, 121-131.
Blair, L.A.C., K.K. Bence and J. Marshall. (2000) GFP in the Study of Neuronal Signalling Pathways. Current Protocols Neurosci., vol. 5.15.
Blair, L.A.C., K.K. Bence, T. Franke, D. Kaplan and J. Marshall (1999) Akt-dependent potentiation of L channels by IGF 1 is required for neuronal survival. J. Neuroscience 19, 1940-51.
Garcia, E.P., Mehta, S., Blair, L.A.C., Wells, D.G., Shang, J., Fukushima. T., Fallon, J.R., Garner, C.C., and Marshall, J. (1998) SAP90 binds and clusters kainate receptors causing incomplete desensitization. Neuron 21, 727-39.
Blair, L.A.C., K.K. Bence and J. Marshall. (1998) The jellyfish green fluorescent protein: a tool for studying ion channels and second messenger signalling in neurons. Meth.Enzymol., 302, 213-25.
Blair, L.A.C. and Marshall, J. (1997) IGF-1 modulates N- and L-calcium channels in a Pl 3-kinase-dependent manner. Neuron 19, 421-429.
Moss, G.W.J., Marshall, J., Morabito, M., Howe, J.R. and Moczydlowski, E.G. (1996) An Evolutionarily Conserved Binding Site for Serine Proteinase Inhibitors in Large Conductance Calcium-Activated Potassium Channels. Biochemistry 35, 16024-16035.

(56) References Cited

OTHER PUBLICATIONS

Moss, G.W.J., Marshall, J. and Moczydlowski, E. (1996) A serine Proteinase-like Domain at the C-terminus of Slowpoke Calcium-activated Potassium channels. J.Gen.Physiol. 108, 473-484.

Marshall, J., Molloy, R., Moss, G., Howe, J.R., Hughes, T.E. (1995) The Jellyfish Green Fluorescent Protein: A new tool for studying ion channel expression. Neuron 14, 211-215.

Kishino, T., Lalande, M., and Wagstaff, J. (1997). UBE3A/E5-AP mutations cause Angelman syndrome. Nat. Genet. 15, 70-73.

Albrecht, U., Sutcliffe, J.S., Cattanach, B.M., Beechey, C.V., Armstrong, D., Eichele, G., and Beaudet, A.L. (1997). Imprinted expression of the murine Angelman syndrome gene, Ube3a, in hippocampal and Purkinje neurons. Nat. Genet. 17, 75-78.

Minichiello, L., Calella, A.M., Medina D.L., Bonhoeffer, T., Klein, R., and Korte, M. (2002). Mechanism of TrkB-mediated hippocampal long-term potentiation. Neuron 36, 121-137.

Minichiello, L., (2009). TrkB signaling pathways in LTP and learning. Nature 10, 850-860.

Dan, B. (2009). Angelman syndrome: Current understanding and research prospects. Epilepsia 50:11, 2331-2339.

\* cited by examiner

LONG TERM POTENTIATION WITH CYCLIC-GLUR6 ANALOGS

CROSS REFERENCE TO RELATED APPLICATIONS

This application is a national phase application of, and claims priority to, PCT/US2010/046891, filed on Aug. 27, 2010, which claims the benefit of priority under 35 U.S.C. §119(e) to U.S. Patent Application No. 61/237,341 filed on Aug. 27, 2009, the disclosures of which are incorporated herein by reference in their entirety.

FIELD OF THE INVENTION

This invention employs a composition (shown below) that facilitates the induction of long-term potentiation (LTP). Without being bound by any particular theory, it is believed that LTP is the cellular manifestation of learning and memory.

The composition (one analog of which is termed CN2097) is a reversible modulator of at least one neuron-specific PDZ domain comprising

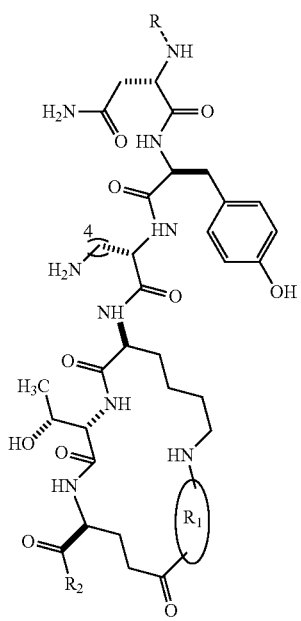

Structure 5 wherein
R is a molecular transporter with or without a linker amino acid;
$R_1$ is at least about one amino acid covalently bound; and, $R_2$ is isoleucine, leucine, alanine, phenylalanine, or valine, and methods of use.

Disruptions in LTP lead to disruptions in memory and has been associated with several neurological disorders, including autism syndromes and neurodegenerative disorders. The application of CN 2097 during the induction of LTP with a stimulus that is normally insufficient, results in the successful induction of LTP.

BACKGROUND OF THE INVENTION

There are currently no treatments available that facilitate LTP and there are no clinical trials of such products. LTP failure is implicated in Angelman Syndrome. Without being bound by any particular theory, it is believed that Angelman syndrome (AS) is a neuro-genetic disorder characterized by intellectual and developmental delay, sleep disturbance, seizures, jerky movements especially hand-flapping, frequent laughter or smiling, and usually a happy demeanor. Some in the art believe that AS is a classic example of genetic imprinting in that it is usually caused by deletion or inactivation of genes on the maternally inherited chromosome 15. The related syndrome, Prader-Willi syndrome, is believed caused by a similar loss of paternally-inherited genes.

CN2097 and related compounds are presented in U.S. Provisional Patent Application Ser. No. 61/179,055, entitled "Cyclic-GluR6 Analogs, Methods of Treatment and Use" (Spaller et al.) the teachings of which are incorporated herein by reference in their entirety. CN 2097 is a peptidomimetic drug that selectively targets the PDZ binding domain of the PSD-95, a scaffolding protein involved in the development and regulation of neuronal synapses CN 2097 has demonstrated specificity for the NMDA receptor 2B (NR2B) subunit. The association of PSD-95 with NMDA receptors is an element in the propagation of the synaptic changes of LTP and long-term depression (LTD) that induce learning and memory. PSD-95 is a member of the MAGUK-family of PDZ domain-containing proteins. Its basic structure includes three PDZ domains, an SH3 domain, and a guanylate kinase-like domain (GK).

Angelman syndrome is a result of loss-of-function mutations or deletions in the maternally inherited allele of UBE3A. Mice that are deficient in maternal Ube3a also show genetically reversible deficits in learning and the induction of hippocampal long-term potentiation (LTP)[1-3], a form of synaptic plasticity. Angelman syndrome (AS) is caused by disruptions in function due to mutations and/or deletions in the maternally inherited allele of an E3 ubiquitin ligase, UBE3A, a gene that has also been implicated in the broader spectrum of Autism patients. A mouse model for AS carries the maternally inherited Ube3a-null mutation and shows profound impairments in hippocampal synaptic plasticity as seen in FIG. 8. It has been reported that UBE3A is also required for experience dependent maturation in the visual cortex. In particular, AS mice show deficits in long-term potentiation (LTP) and long-term depression (LTD), which are the cellular substrates of learning and memory. These forms of synaptic plasticity are highly regulated by activity-dependent changes in the ratio of NMDA subunits, specifically NR2A and NR2B subunits. NMDA receptors gate the influx of calcium ions across the post-synaptic membrane. Depending on the characteristics of the calcium influx generated in response to pre-synaptic activity, either LTP or LTD can be induced. This calcium influx activates calcium-dependent enzymes such as CaMKII, which has been strongly implicated in Angelman syndrome, and triggers its autophosphorylation at Thr286. This autophosphorylation is very important as it allows the enzyme to remain active once the calcium levels return to normal. This pathway requires an interplay between the NMDA receptor, CaMKII and a post-synaptic scaffolding protein (PSD-95 in particular), which brings these biochemical elements into proximity. Thr286 autophosphorylation is instrumental in promoting the association of CaMKII with the PSD by directly binding to the NMDA receptor. Interestingly, there is also a secondary inhibitory autophosphorylation at Thr305/306 that has been suggested to regulate the association of CaMKII to the PSD. Interplay between these states can govern the availability of CaMKII to regulate synaptic plasticity in response to calcium influx during learning and memory activity. The clinical features of AS have been linked to the misregulation of alpha CaMKII function. The role of CaMKII in synaptic plasticity and AS has been investigated at the synapses of the Schaffer-collateral-CA1 pyramidal cells in the adult hippocampus.

Noted is the Szeto-Schiller (SS) peptide (Dmt-D-Arg-Phe-Lys-NH2; where Dmt=2',6'-dimethyltyrosine). This represents an approach with targeted intracellular delivery, including to the inner mitochondrial membrane. The structural motif of the SS peptide centers on alternating aromatic residues and basic amino acids (aromatic-cationic peptides). They are small, easy to synthesize, readily soluble in water, and resistant to peptidase degradation. The presence of a D-amino acid in either the first or second position renders them resistant to aminopeptidase activity, and amidation of the C-terminus reduces hydrolysis from the C-terminus. Despite carrying 3+ net charge at physiological pH, these peptides have been reported to readily penetrate cell membranes of a variety of cell types. This is further set forth in Zhao K, Luo G, Zhao G M, Schiller P W, Szeto H H. Transcellular transport of a highly polar 3+ net charge opioid tetrapeptide. *J Pharmacol Exp Ther.* 2003; 304:425-432. PubMed DOI: 10.1124/jpet.102.040147

Noted are neurotrophins. Neurotrophins are a family of neurotrophic factors involved in the development, maintenance, and repair of the nervous system. The neurotrophin family consists of nerve growth factor (NGF), brain-derived neurotrophic factor (BDNF), neurotrophin-3 (NT-3) and NT-4/5. The neurotrophins are believed to bind to and activate Trk family proteins, the receptor tyrosine kinases (RTK), to exert their effects. NGF binds to TrkA, BDNF and NT-4/5 bind to TrkB, and NT-3 binds to TrkC. The neurotrophins BDNF and NGF and their high-affinity receptor Trk receptor are reported as widely expressed in neurons throughout the central nervous system. Binding of neurotrophins to Trk receptor is reported to result in phosphorylation of tyrosine residues in the cytoplasmic domain of the receptor and subsequent recruitment and activation of various signaling adaptor proteins, including Shc, Gab1, and shp2. Attention is drawn to the following publications the teachings of which are incorporated herein by reference in their entirety as are all references cited herein.

1. Jiang, Y.-h. et al. Mutation of the Angelman Ubiquitin Ligase in Mice Causes Increased Cytoplasmic p53 and Deficits of Contextual Learning and Long-Term Potentiation. *Neuron* 21, 799-811 (1998).
2. Weeber, E. J. et al. Derangements of Hippocampal Calcium/Calmodulin-Dependent Protein Kinase II in a Mouse Model for Angelman Mental Retardation Syndrome. *J. Neurosci.* 23, 2634-2644 (2003).
3. van Woerden, G. M. et al. Rescue of neurological deficits in a mouse model for Angelman syndrome by reduction of [alpha]CaMKII inhibitory phosphorylation. *Nat Neurosci* 10, 280-282 (2007).
4. Yi, J. J. & Ehlers, M. D. Emerging Roles for Ubiquitin and Protein Degradation in Neuronal Function. *Pharmacol Rev* 59, 14-39 (2007).
5. Yi, J. J. & Ehlers, M. D. Ubiquitin and Protein Turnover in Synapse Function. *Neuron* 47, 629-632 (2005).
6. Elgersma, Y. et al. Inhibitory Autophosphorylation of CaMKII Controls PSD Association, Plasticity, and Learning. 36, 493-505 (2002).
7. Elgersma, Y., Sweatt, J. D. & Giese, K. P. Mouse Genetic Approaches to Investigating Calcium/Calmodulin-Dependent Protein Kinase II Function in Plasticity and Cognition. *J. Neurosci.* 24, 8410-8415 (2004).
8. Walz N C, B. G. Sensory processing patterns in persons with Angelman syndrome. *Am J Occup Ther.* 60, 472-9 (2006).
9. Charles, A. W. et al. Angelman syndrome 2005: Updated consensus for diagnostic criteria. *American Journal of Medical Genetics Part A* 140A, 413-418 (2006).
10. Oh-Nishi, A., Saji, M., Satoh, S. Z., Ogata, M. & Suzuki, N. Late phase of long-term potentiation induced by co-application of N-methyl-d-aspartic acid and the antagonist of NR2B-containing N-methyl-d-aspartic acid receptors in rat hippocampus. Neuroscience 159, 127-135 (2009).
11. Yashiro, K. et al. Ube3a is required for experience-dependent maturation of the neocortex. *Nat Neurosci* advanced online publication (2009).
12. Liu, L. et al. Role of NMDA receptor subtypes in governing the direction of hippocampal synaptic plasticity. *Science* 304, 1021-4 (2004).
13. Mallon, A. P., Auberson, Y. P. & Stone, T. W. Selective subunit antagonists suggest an inhibitory relationship between NR2B and NR2A-subunit containing N-methyl-D:—aspartate receptors in hippocampal slices. *Exp Brain Res* 162, 374-83 (2005).
14. Massey, P. V. et al. Differential Roles of NR2A and NR2B-Containing NMDA Receptors in Cortical Long-Term Potentiation and Long-Term Depression. *J. Neurosci.* 24, 7821-7828 (2004).
15. Morris, R. Developments of a water-maze procedure for studying spatial learning in the rat. *Journal of Neuroscience Methods* 11, 47-60 (1984).
16. Bienenstock, E. L., Cooper, L. N. & Munro, P. W. Theory for the development of neuron selectivity: orientation specificity and binocular interaction in visual cortex. *J. Neurosci.* 2, 32-48 (1982).
17. Giese, K. P., Fedorov, N. B., Filipkowski, R. K. & Silva, A. J. Autophosphorylation at Thr286 of the Alpha} Calcium-Calmodulin Kinase II in LTP and Learning. Science 279, 870-873 (1998).
18. Shen, K. & Meyer, T. Dynamic Control of CaMKII Translocation and Localization in Hippocampal Neurons by NMDA Receptor Stimulation. *Science* 284, 162-167 (1999).
19. Mallon, A., Auberson, Y. & Stone, T. Selective subunit antagonists suggest an inhibitory relationship between NR2B and NR2A-subunit containing N-methyl-d-aspartate receptors in hippocampal slices. *Experimental Brain Research* 162, 374-383 (2005).
20. Hardingham, G. E., Fukunaga, Y. & Bading, H. Extrasynaptic NMDARs oppose synaptic NMDARs by triggering CREB shut-off and cell death pathways. *Nat Neurosci* 5, 405-14 (2002).
21. Quinlan, E. M., Olstein, D. H. & Bear, M. F. Bidirectional, experience-dependent regulation of N-methyl-d-aspartate receptor subunit composition in the rat visual cortex during postnatal development. *Proceedings of the National Academy of Sciences of the United States of America* 96, 12876-12880 (1999).
22. Needleman and J. Marshall CamKII phosphorylation of PSD-95 regulates synaptic kainate receptor localization. Submitted.
23. Jeyifous, O. N., L A; Fujisawa, S; Aoki, C; Garner, C C; Marshall, J and Green W N. A role of SAP97 in NMDA receptor sorting and trafficking submitted.
24. Salinas, G. D., L. A. C. Blair, L. A. Needleman, J. D. Gonzales, Y. Chen, M. Li, J. D. Singer and J. Marshall. Actinfilin is a Cul3 substrate adaptor, linking GluR6 kainate receptor subunits to the ubiquitin-proteasome pathway. *J. Biol. Chem.* 281(52):40164-73.
25. Gao, L., L. A. C. Blair, G. D. Salinas, L. A. Needleman and J. Marshall. (2006). IGF-1-modulation of CaV1.3 calcium channels depends on $Ca^{+2}$ release from $IP_3$-senstive 25. stores and CaMKII-phosphorylation of the alpha1 subunit EF hand. *J. Neurosci.* 26, 6259-68.
26. Gao, L., L. A. C. Blair and J. Marshall. (2006). CaMKII-independent effects of KN93 and its inactive analog KN92: reversible inhibition of L-type calcium channels. *Biochem. Biophys. Res. Comm.* 354, 1606-10.
27. Wang X, Tang X, Li M, Marshall J, Mao Z. (2005) Regulation of neuroprotective activity of myocyte-enhancer factor 2 by cAMP-protein kinase A signaling pathway in neuronal survival. *J. Biol. Chem* 280, 16705-13.
28. Piserchio, A., Spaller, M., Marshall, J., and Mierke, D. F (2004) Targeting specific PDZ domains of PSD-95: Structural basis for enhanced affinity and enzymatic stability of a cyclic peptide Chemistry&Biology 11, 468-473.
29. Ren, Z., Riley, N., Needleman, L., Sanders J M, Swanson G T, Marshall J. (2003) Cell surface expression of GluR5 kainate receptors is regulated by an endoplasmic reticulum retention. *J. Biol. Chem.* 26; 278(52):52700-9.
30. Marshall J, Dolan B M, Garcia E P, Sathe S, Tang X, Mao Z, Blair L. A. C. (2003) Calcium channel and NMDA receptor activity differentially regulate nuclear C/EBP levels to control neuronal survival. *Neuron* 39: 625-629.
31. Ren Z, Riley N J, Garcia E P, Sanders J M, Swanson G T, Marshall J. (2003) A Trafficking Checkpoint Controls Kainate Receptor Heterodimerization. *J. Neuroscience* 23, 6608-16.
32. Gong, X., Tang, X., Wiedmann, M., Wang, X., Peng, J., Zheng, D., Blair, L. A. C., Marshall, J., and Mao, Z (2003) Cdk-5-mediated inhibition of the protective effects of transcription factor MEF2 in neurotoxicity-induced apoptosis. *Neuron* 38:33-46.
33. Bowie, D., Garcia, E. P., Marshall, J., Traynelis, S. F. and Lange, G. David (2003) Allosteric Regulation and Spatial Distribution of Kainate Receptors Bound to Ancillary Proteins. *J Physiol.* 547:373-85.
34. Piserchio, A., Pellegrini, M., Mehta, S., Blackman, S. M., Garcia, E. P., Marshall, J., and Mierke, D. F (2002) Structural Characterization of the Intermolecular Interaction of SAP90 with the GluR6-subunit of Kainate Receptors *J. Biol. Chem.* 277: 6967-6973.
35. Mehta, S., Wu, H., Garner, C. C., and Marshall, J (2001) Intramolecular interactions regulate SAP97 binding to kainate receptors. *J. Biol. Chem.* 276: 16092-16099.
36. Savinainen, A., Garcia, E. P., Dorow, D., Marshall, J., and Liu, Y-F (2001) Kainate Receptor Activation Induces Mixed Lineage Kinase-mediated Cellular Signaling Cascades via Post-synaptic Density Protein 95 *J. Biol. Chem.* 2001 276: 11382-11386.
37. Fukushima T., Shingai. R., and Marshall, J (2001) Calcium inhibits Willardiine-induced responses in kainate receptor GluR6(Q) and GluR6(Q)/KA-2 *Neuroreport* 12 163-167.
38. Liu, Y-F., Sudol, M., Marshall, J (2000) Assignment of molecular mechanisms of neuronal death underlying Huntington's disease. *J. Biol. Chem.* 275, 19035-19040.
39. Bence. K. K., Blair, L. A. C., and J. Marshall. (2000) Potentiation of neuronal L calcium channels by IGF-1 requires phosphorylation of the 1 subunit on a specific tyrosine residue. *Neuron* 27, 121-131.
40. Blair, L. A. C., K. K. Bence and J. Marshall. (2000) GFP in the Study of Neuronal Signalling Pathways. *Current Protocols Neurosci.*, vol. 5.15.
41. Blair, L. A. C., K. K. Bence, T. Franke, D. Kaplan and J. Marshall (1999) Akt-dependent potentiation of L channels by IGF-1 is required for neuronal survival. *J. Neuroscience* 19, 1940-51.
42. Garcia, E. P., Mehta, S., Blair, L. A. C., Wells, D. G., Shang, J., Fukushima. T., Fallon, J. R., Garner, C. C., and Marshall, J. (1998) SAP90 binds and clusters kainate receptors causing incomplete desensitization. *Neuron* 21, 727-39.
43. Blair, L. A. C., K. K. Bence and J. Marshall. (1998) The jellyfish green fluorescent protein: a tool for studying ion channels and second messenger signalling in neurons. *Meth. Enzymol.*, 302, 213-25.
44. Blair, L. A. C. and Marshall, J. (1997) IGF-1 modulates N- and L-calcium channels in a PI 3-kinase-dependent manner. *Neuron* 19, 421-429.
45. Moss, G. W. J., Marshall, J., Morabito, M., Howe, J. R. and Moczydlowski, E. G. (1996) An Evolutionarily Conserved Binding Site for Serine Proteinase Inhibitors in Large Conductance Calcium-Activated Potassium Channels. *Biochemistry* 35, 16024-16035.
46. Moss, G. W. J., Marshall, J. and Moczydlowski, E. (1996) A serine Proteinase-like Domain at the C-terminus of Slowpoke Calcium-activated Potassium channels. *J. Gen. Physiol.* 108, 473-484.
47. Marshall, J., Molloy, R., Moss, G., Howe, J. R., Hughes, T. E. (1995) The Jellyfish Green Fluorescent Protein: A new tool for studying ion channel expression. *Neuron* 14, 211-215.
48. Kishino, T., Lalande, M., and Wagstaff, J. (1997). UBE3A/E5-AP mutations cause Angelman syndrome. *Nat. Genet.* 15, 70-73.
49. Albrecht, U., Sutcliffe, J. S., Cattanach, B. M., Beechey, C. V., Armstrong, D., Eichele, G., and Beaudet, A. L. (1997). Imprinted expression of the murine Angelman syndrome gene, Ube3a, in hippocampal and Purkinje neurons. *Nat. Genet.* 17, 75-78.
50. Jiang, Y., Armstrong, D., Albrecht, U., Atkins, C. M., Noebels, J. L., Eichele, G., Sweatt, D., and Beaudet, A. L., (1998). Mutation of the Angelman ubiquitin ligase in mice causes increased cytoplasmic p53 and deficits of contextual learning and long-term potentiation. Neuron 21, 799-811.
51. Minichiello, L., Calella, A. M., Medina D. L., Bonhoeffer, T., Klein, R., and Korte, M. (2002). Mechanism of TrkB-mediated hippocampal long-term potentiation. Neuron 36, 121-137.
52. Minichiello, L., (2009). TrkB signaling pathways in LTP and learning. Nature 10, 850-860.
53. Dan, B. (2009). Angelman syndrome: Current understanding and research prospects. Epilepsia 50:11, 2331-2339.

SUMMARY OF THE INVENTION

Figure 1:
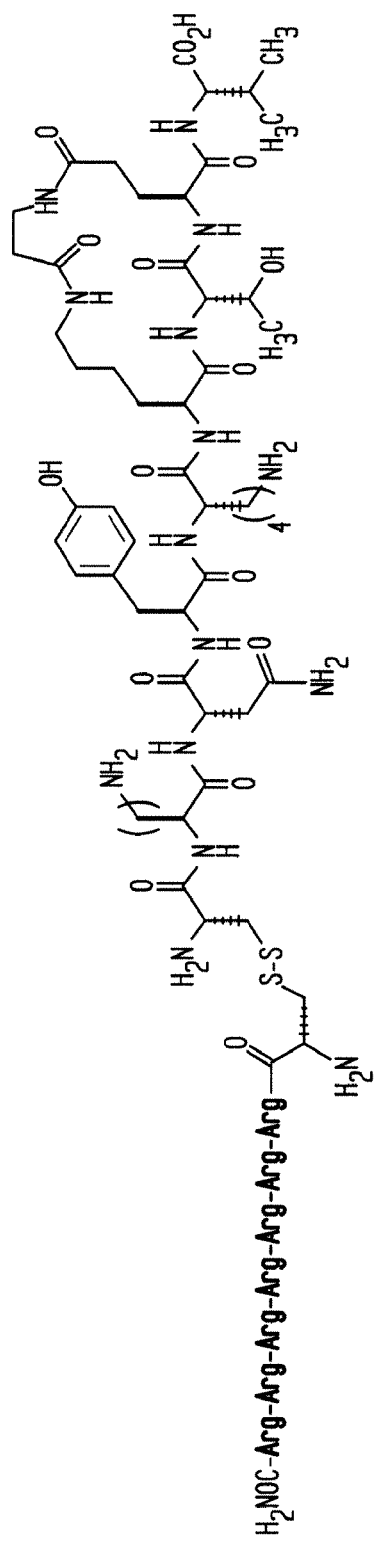
FIG. 1 is a representation of CN2097.

This invention includes inducing long-term potentiation in a subject by the method of administering a therapeutically effective dose of a CN2097-like compound. In some embodiments the method employs dosage is from about 1 mg/Kg to about 10 mg/Kg, and particularly from about 4 mg/Kg to about 6 mg/Kg, with particular reference to about 5 mg/Kg.

In specific embodiments the method of the invention employs dosages which establish a blood and CNS level of about 0.1 to about 10 µM, with particular reference to about 2 µM to about 4 µM.

The method usefully employs CN2097.

Additionally and without being bound by any particular theory, CN 2097 may induce its therapeutic effects by the modulation of other PDZ domains, including, but not limited to, Shank, S-SCAM, Pick, GRIP and MAGI.

In yet another embodiment this invention discloses a method of treating conditions selected from the group consisting of Angelman Syndrome, Alzheimer's Disease, cognitive disorders, learning disorders, or autism spectrum disorders by facilitating the induction of Long-Term Potentiation and Long-term Depression in a subject by the method of administering a therapeutically effective dose of a CN2097-like compound.

Ube3a deficient ("AS") mice were developed previously (Jiang, Y. H. et al. Mutation of the Angelman ubiquitin ligase in mice causes increased cytoplasmic p53 and deficits of contextual learning and long-term potentiation. Neuron 21, 799-811 (1998)), were obtained through the Jackson Laboratory. Mice were bred on a 129S7 background. To obtain heterozygous mice lacking the Ube3a gene maternally (m−/p+), we crossed a heterozygous female mouse (m−/p+) with a wild-type male mouse (m+/p+). Wild type (WT) littermates (m+/p+) were used as controls.

DETAILED DESCRIPTION OF THE INVENTION

This invention will be better understood with resort to the following definitions.

A. Cyclic-GluR6 Analogs (CN2097-like compounds) shall mean a composition which is reversible inhibitor of at least one neuron-specific PDZ domain comprising

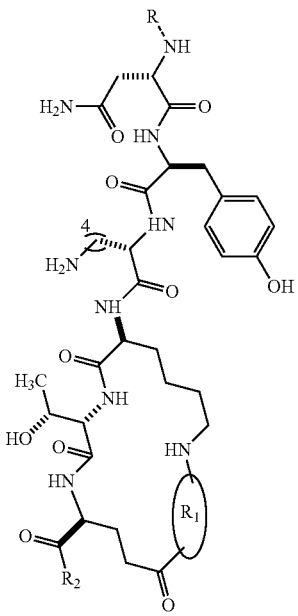

Structure 5 wherein

R is a molecular transporter with or without a linker amino acid;

$R_1$ is at least about one amino acid covalently bound; and, $R_2$ is isoleucine, leucine, alanine, phenylalanine, or valine.

B. Long-Term Potentiation (LTP) shall mean a persistent increase in synaptic strength following stimulation of a chemical synapse, including high frequency, chemical, sensory stimulation or as a result of brain activity. "Persistent" in this context shall mean for at least about 30 minutes in-vitro, and with the potential to last indefinitely in-vivo.

The co-application of CN 2097 along with electrical pulses induces LTP in neuronal cells that would normally not be induced, which is a 2-step regimen of drug and pulses. In one embodiment, post-dosing LTP is induced with three, one second, 100 Hz pulses of current 10 seconds apart. Without being bound by any particular theory, it is believed that the therapeutic regimen alters (lowers) the experience dependent threshold for the consolidation and acquisition of memory and thus learning. In disorders of memory this drug enhances the encoding of information and skills into long term memory. In addition it is believed to bolster working memory, having a dual effect in both short-term and long-term memory.

In a particular embodiment, this method treats Angelman Syndrome. CN 2097 is a peptidomimetic drug that selectively targets the PDZ binding domain of the PSD-95, a scaffolding protein involved in the development and regulation of neuronal synapses. It is further contemplated as treating neurological conditions characterized by deficits in cognition (primary or co-morbidity) such as schizophrenia, Alzeheimer's disease, Fragile –X syndrome, autism and "life style" drug damage (e.g., methamphetamine, PCP, cocaine etc). The NMDA receptor 2B (NR2B) subunit is involved in learning and memory, including its cellular correlatives, LTP and LTD. CN 2097 was able to lower the threshold for experience-dependent synaptic plasticity. Specifically, an LTP sub-threshold induction protocol that normally does not produce LTP was repeated in the presence of CN 2097 and LTP was elicited. Thus, CN 2097 was able to increase the likelihood that the lower level of stimulation elicited the learning response. Note that synaptic plasticity is where a synaptic signaling event induces a significant and persistent change in synaptic strength, i.e. Increase=LTP, decrease=LTD. A persistent (greater than 30 minutes post HFS) increase or decrease of at least 10% is generally understood to be significant as compared to baseline (100%) fEPSP slope recordings.

Figure 10:
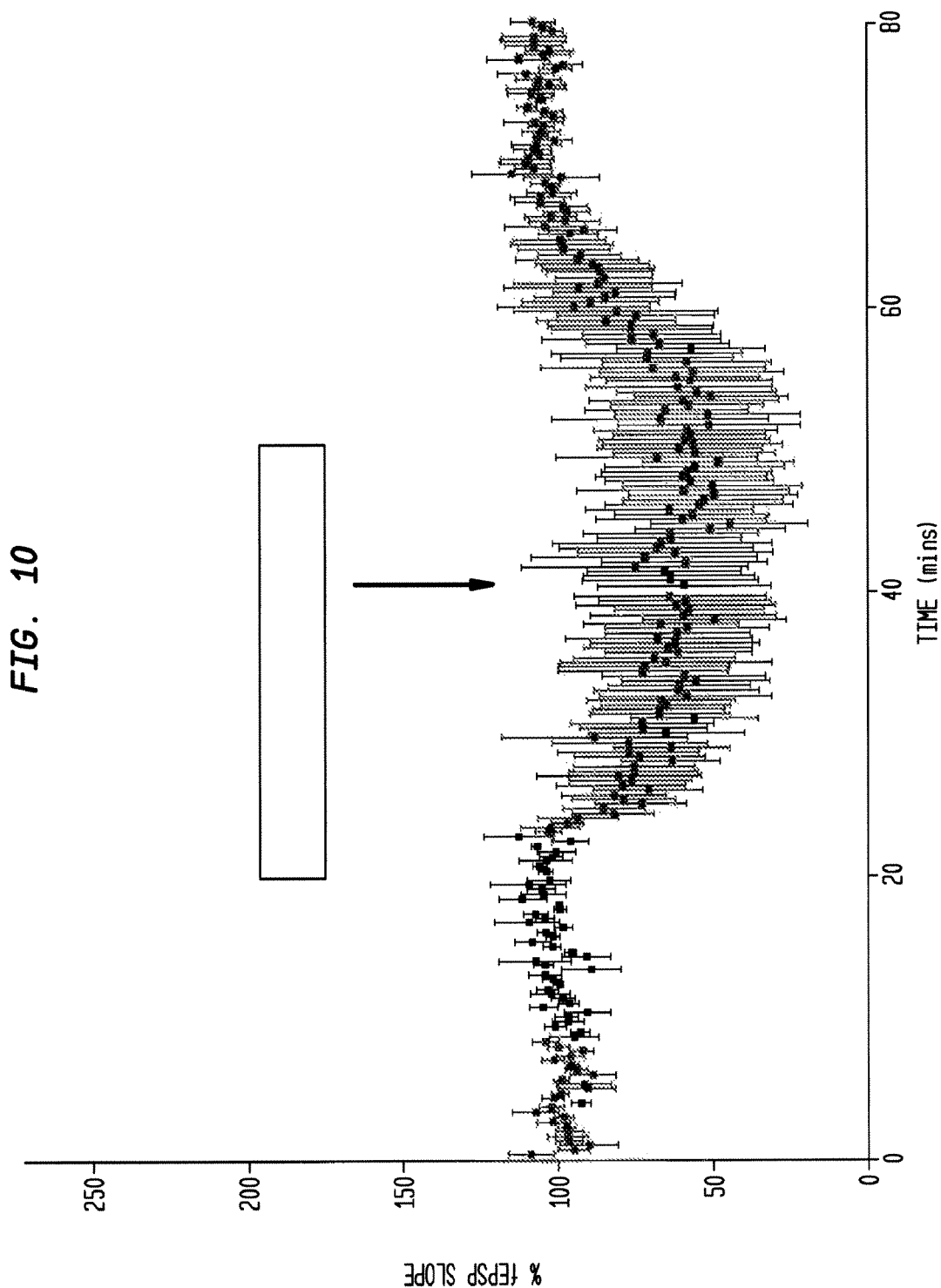
FIG. 10 displays data from WT mouse szeto-CN2097 (analogue, with Poly Arginine delivery moiety replaced by the 'szeto' sequence), treatment 2 µM, combined with HFS1, no LTP was observed, averaged responses at 70-80 minutes were 101.9+/−0.79% of baseline, n=4.

Attention is further drawn to the szeto(SS) peptide analogue of CN 2097 (having szeto instead of the poly-Arg tail); CN5135, and tat-NR2B9c (TAT) whose activity is shown in FIG. 10. Note is made of extrasynaptic receptor populations. By way of non-limiting examples these include $GABA_A$ including subunits $\alpha 5\beta\gamma$ and/or $\alpha 4\beta\delta$, glutamate NR2B and NR2A subunit containing NMDA receptors.

In Angelman Syndrome, changes in the insertion of NR2B and NR2A subunits to the synapse or an alteration in their downstream signaling is thought to decrease the probability of synaptic plasticity induction otherwise produced in normal subjects. Deficits in the induction of synaptic plasticity (LTP and LTD) underlie the learning problems in patients. This in turn increases learning problems. Without being bound by any particular theory it is believed that CN 2097 will lower synaptic plasticity threshold and rescue deficits in LTP, cure the learning deficits and provide an effective treatment for Angelman Syndrome patients.

Using Fmoc-based protocols, a series of peptide ligands were synthesized that complement the PDZ-binding domain of PSD-95 with the criteria of being membrane permeable, resistant to protease activity and biologically active. The peptide KNYKKTEV, which codes for the CRIPT PDZ-3 binding motif, was cyclized between the valine (V) and threonine (T) residues via beta-alanine linkage and either myristylated (CN2180) or linked to a poly-arginine tail (CN2097; FIG. 1) to enhance its diffusion and uptake capacity by neurons in intact tissues. Binding specificity of CN2180 was tested against a PDZ-domain array consisting of 96 distinct His-tagged PDZ domains purified and spotted on a gridded nylon membrane. CN2180 showed high specificity to the PDZ1-PDZ2 domains and moderate binding to the PDZ3 domain of PSD-95, but did not bind to PDZ domains of other MAGUKS or with other PDZ-containing proteins such as MUPP1, S-SCAM, Shank and spinophilin. In electrophysiological and biochemical preliminary studies CN 2097 demonstrates specificity toward the NR2B NMDAR subunit. CN 2097 acts as competitive ligand for this binding site and as such is able to disrupt the normal binding of NR2B receptors to the PSD.

Also, it is believed that CN2097 disrupts NR2B downstream signaling by displacing signaling effectors attached directly or indirectly to the NR2B/PSD-95 signaling complex including CaMKII. Excitotoxic studies suggest that CN 2097 is neuroprotective in both the retina and the hippocampus against lethal doses of NMDA. Without being bound by any particular theory, this effect is believed due to the disruption of apoptotic and necrotic cell signaling pathways that propagate the cell death signal.

Neutrophin signaling proteins are believed to link Trk activation to Ras and the downstream activation of mitogen-activated protein kinases (MAPKs) and the phosphatidylinositol 3-kinase (PI3K)-Akt kinase pathway. Inhibition of p-JNK in particular is a pro-survival effect. JNK is a cell death signaling protein.

Additionally, upregulation of CaMKII, an NMDAR-PSD-95 associated protein, is believed to be associated with synaptic plasticity. Biochemical analyses using western blots of in vivo injected retinas, cultured SH-SY5Y neuroblastomas and primary cultured mouse cerebellar granule neurons (CGN) was undertaken. Left and right eyes were given in vivo injections of phosphate buffered saline (PBS), NMDA, NMDA with CN 2097 and NMDA with CN5135, the retinas were then removed and lysed. CGNs were stimulated by a paradigm designed to mimic synaptic stimulation (1004 glycine, 4004 bicuculline and 404 picrotoxin in ACSF) and SH-SY5Y cells were activated by nerve growth factor (NGF 50 ng/ml). We then probed with antibodies for cell growth and survival pathways and found that 204 CN2097 yielded a variety effects on the mTOR, S6 and AKT expression pathways including increases in both total protein expression and phosphorylation state (CamKII, ERK, AKT1/2, p-S6K, p-S6, p-ERK, p-p38) and inhibiting p-JNK. Additionally CN2097 increased the expression CREB, which is also neuroprotective. Also observed were increases in levels of PSD-95. This data are evidence that CN2097 is proving a neuroprotective effect at the level of the cell death 'master switch'.

tat-NR2B9c (TAT, 2 μM), an established NR2B-PDZ peptidomimetic, did not induce detectable pro-survival signaling changes. Western blot analysis of the effects of CN 2097 in cerebellar granule neurons from injected retinas, primary culture (CGN) and a neuroblastoma cell culture line (SH-SY5Y) demonstrated this to be so. CN2097 (2 μM) was tested after injection into eyes/retinas (lower left panel) applied to cell cultures for 5-30 minutes concurrently with either a synaptic stimulation and nerve growth factor (NGF) 50 ng/ml. CN2097 saw increased ERK, AKT1/2, p-S6K, p-S6, p-ERK, p-p38, p-CREB and PSD-95. Additionally, CN2097 (2 μM) inhibited p-JNK. CN2097S (szeto sequence used instead of Pol-Arginine) and CN5135 (2, 10 and 2004), a structural analogue of CN2097 with disruptive alanine substitutions at the 0 and −2 ring positions (binding domain) were used a negative controls whilst tat-NR2B9c (TAT, 2 μM) was used as a positive control.

ACPD, an agonist of mGluR1, when CN2097 is added leads to an enhancement of PI3K and AKT signaling.

Figure 2:
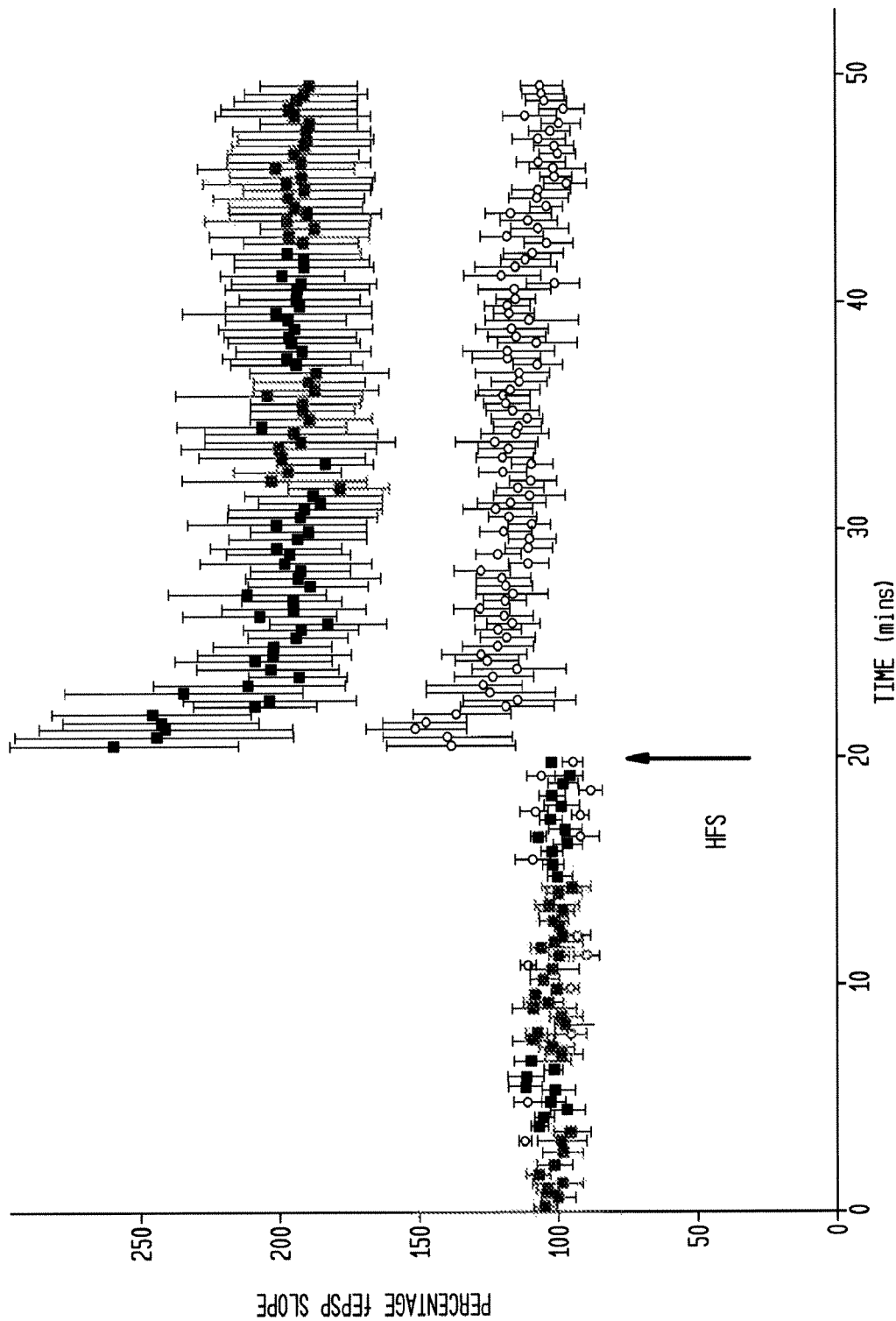
FIG. 2 shows a sub-threshold LTP induction protocol at the adult Wistar rat Schaffer Collateral-CA1 synapse. It would normally induce no increase in baseline fEPSP responses (lower line). As shown, this protocol in the presence of CN2097 2 µM, results in LTP induction (upper line).
Figure 3:
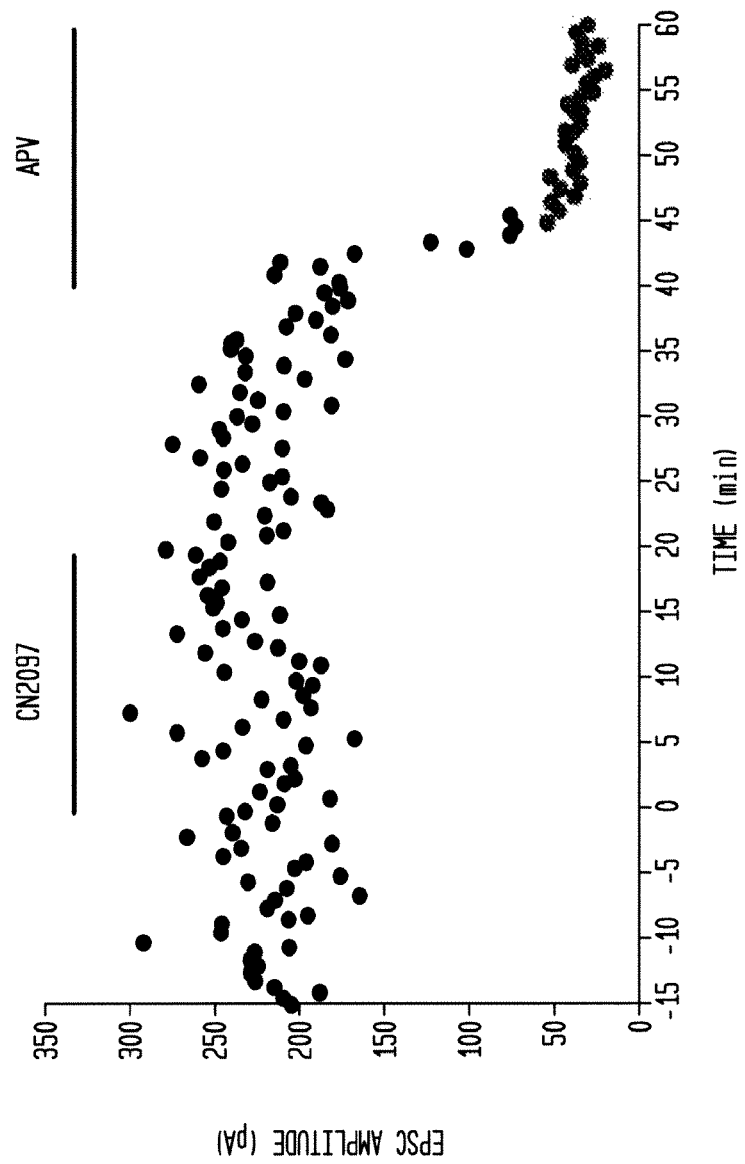
FIG. 3 presents a single, whole cell patch recording of a pharmacologically isolated NMDA excitatory postsynaptic current (EPSC) of a pyramidal neuron in the CA1 region of the hippocampus and the lack of effect upon this current by perfusion of CN2097 2 µM. APV is a selective NMDA receptor antagonist.
Figure 4:
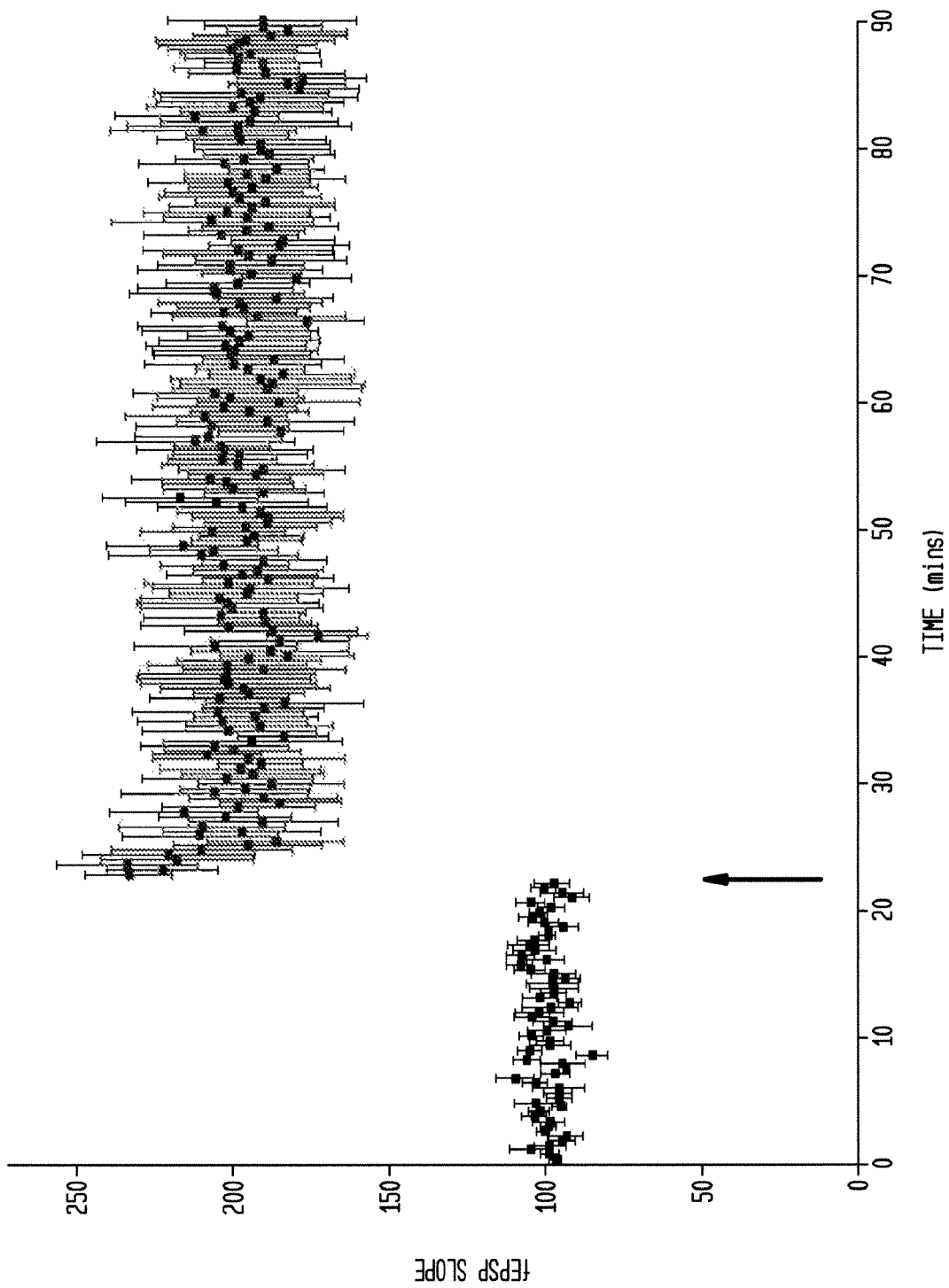
FIG. 4 presents data from a ~2 month WT mouse hippocampal slice, arrow indicates time point at which two High Frequency Stimuli (HFS, 100 pulses in 1 second every 10 ms, i.e. 100 Hz) separated by 15 seconds were applied, resulting in a significant LTP of 200.03+−1.68% averaged over the last ten minutes of the recording (70-80 min), n=4, p<0.05.
Figure 5:
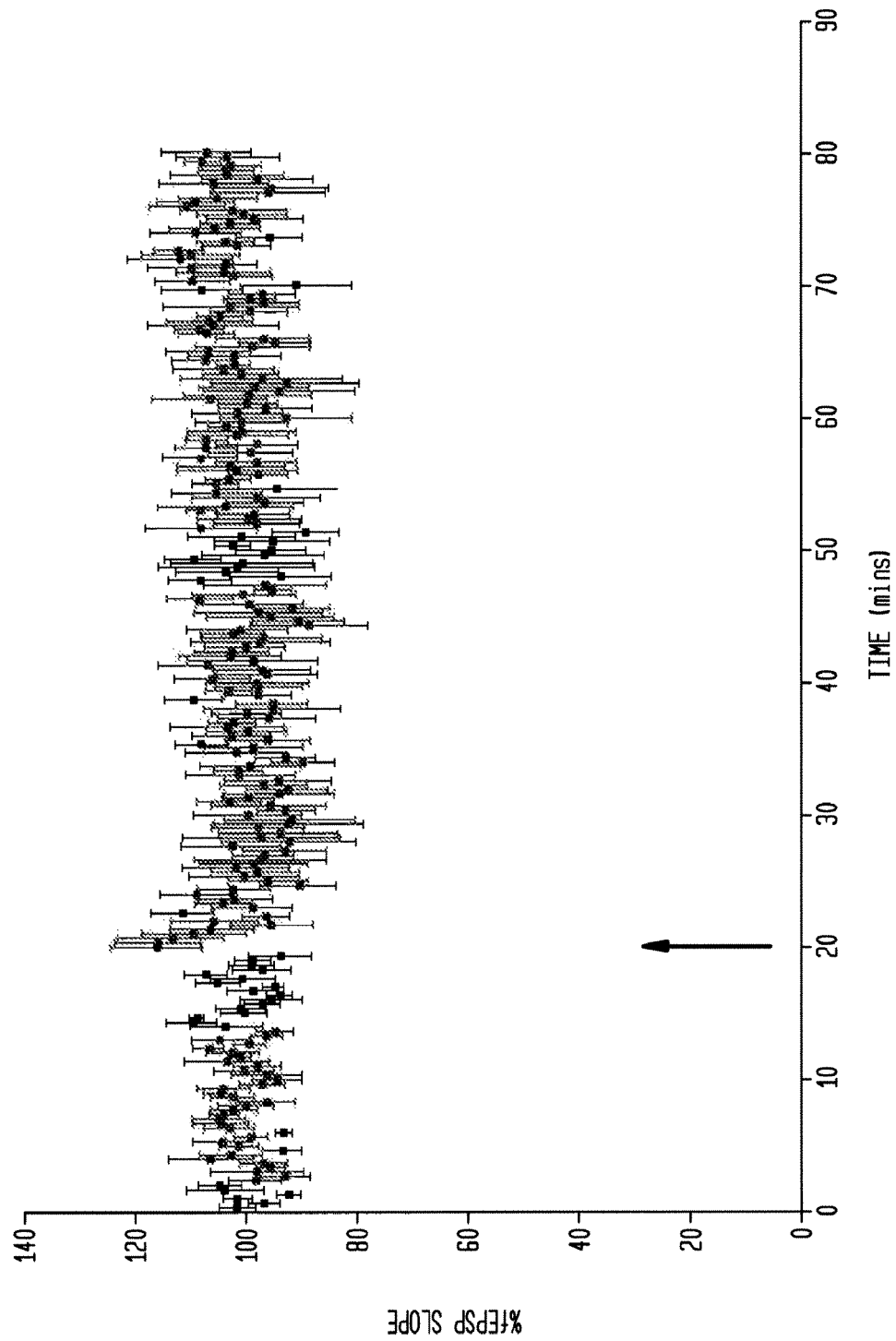
FIG. 5 presents data from a WT mouse hippocampal slice. An arrow indicates the time point at which one, sub-threshold, High Frequency Stimuli (HFS, 100 pulse in 1 second every 10 ms, i.e. 100 Hz) was applied, resulting in no significant change in the synaptic strength, 104+/−0.93%, n=5.
Figure 6:
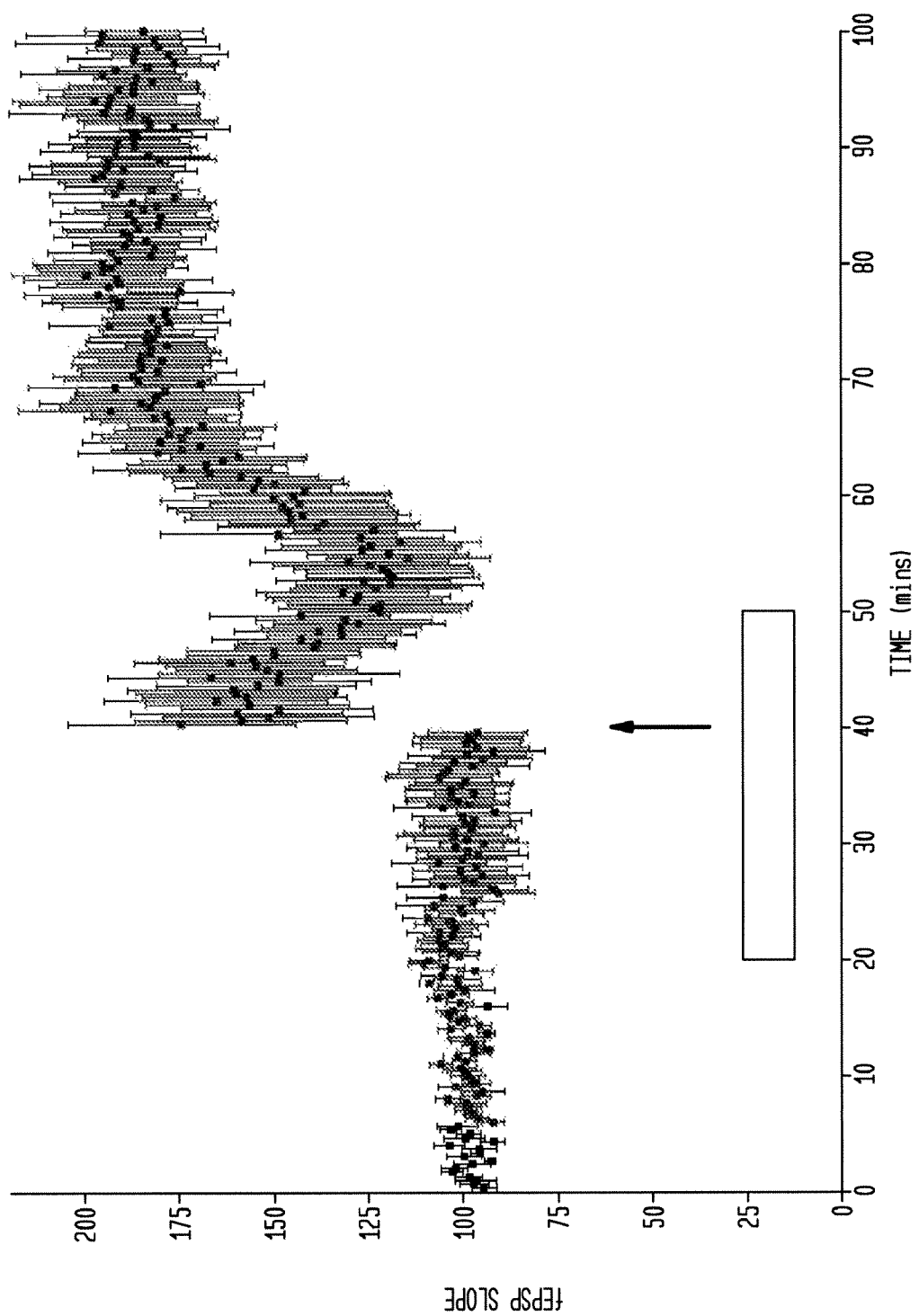
FIG. 6 presents data from a WT mouse adult hippocampal slice. An arrow indicates the time point at which one sub-threshold High Frequency Stimuli (HFS, 100 pulse in 1 second every 10 ms, 100 Hz) was applied. The white box indicates the treatment with CN2097 2 µM. Whilst there is no significant observed effect of CN2097 2 µM alone upon baseline responses between 20 and 40 minutes, the subsequent HFS at 40 minutes results in a significant LTP of 187.2+/−1.034% of baseline fESPS slope, n=7.
Figure 7:
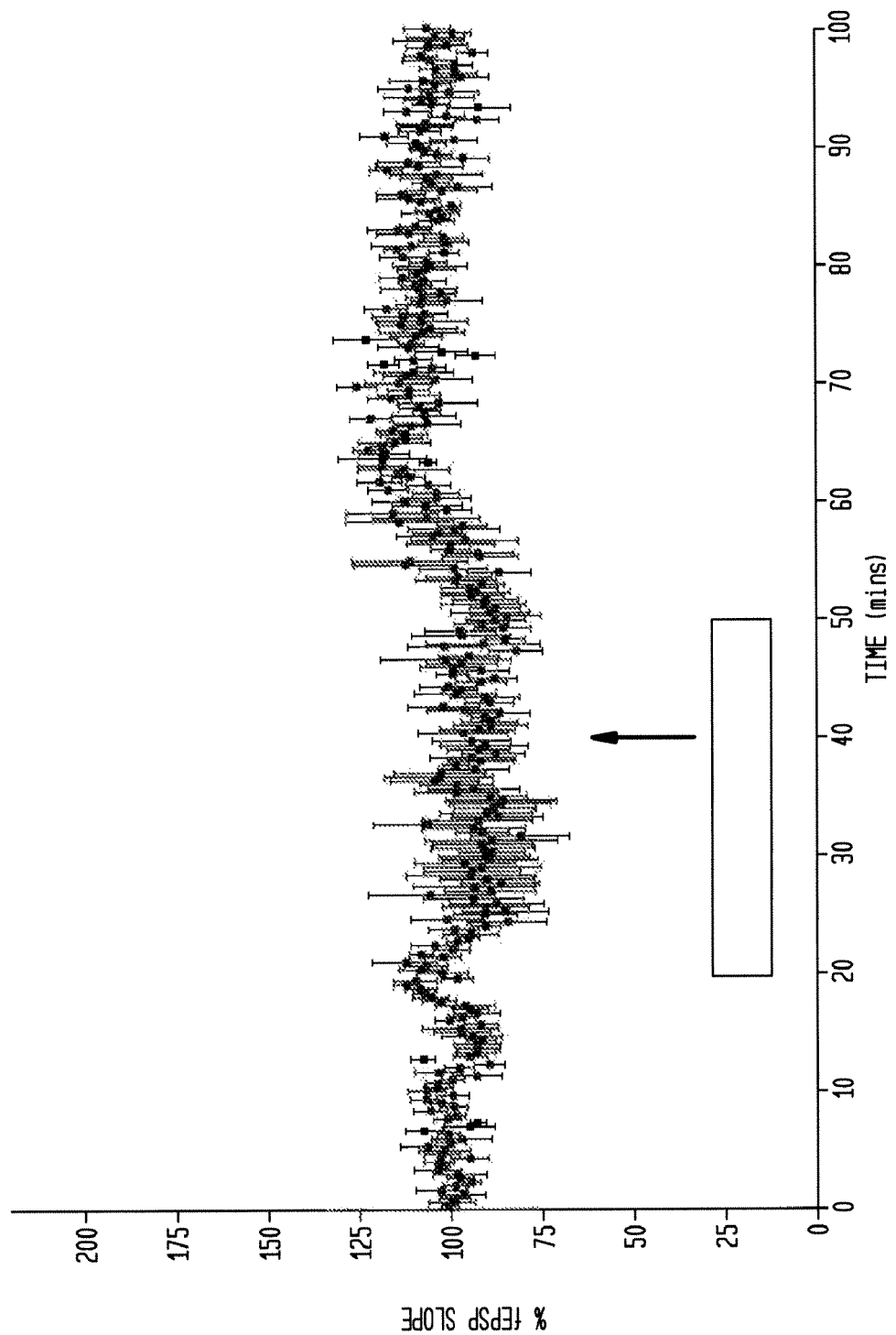
FIG. 7 presents data from a WT mouse, where CN5135 2 µM treatment, combined with HFS1, resulted in no LTP, 103.3%+/−1.085, n=4. CN5135 is a less active analogue of CN2097, with alanine mutations in the 0 and −2 ring positions that contain the posited critical PDZ binding moiety.
Figure 8:
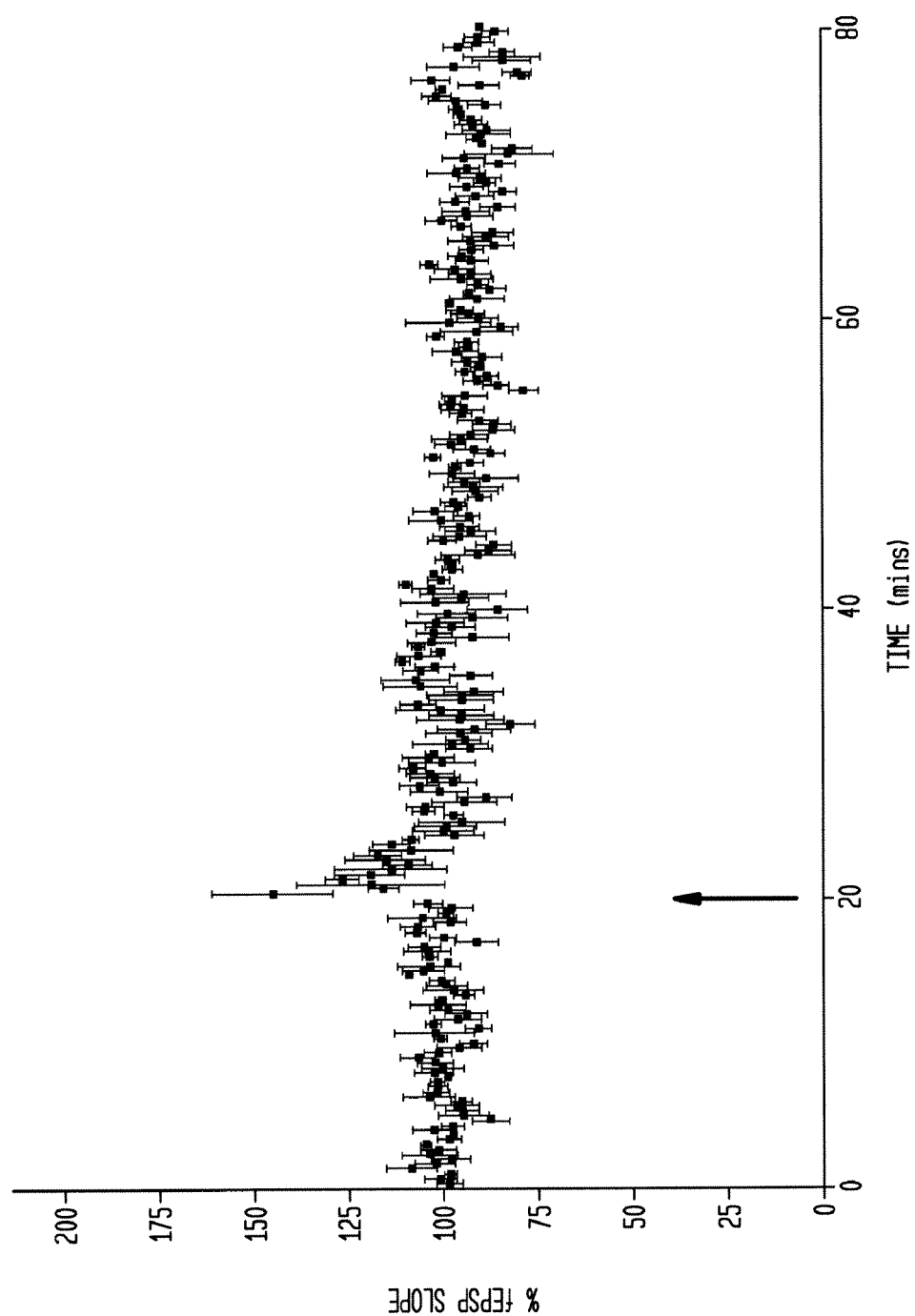
FIG. 8 presents data from an AS mouse (Ube3am−/p+) hippocampal slice. Arrow indicates time point at which three trains of High Frequency Stimuli (HFS, 100 pulse in 1 second every 10 ms, 100 Hz) every 10 seconds, resulting in no significant change in the synaptic strength. At 70-80 minutes the averaged response was 90.33%+/−1.1, n=3. No other stimulation intensities tested induced LTP in AS mice.
Figure 9:
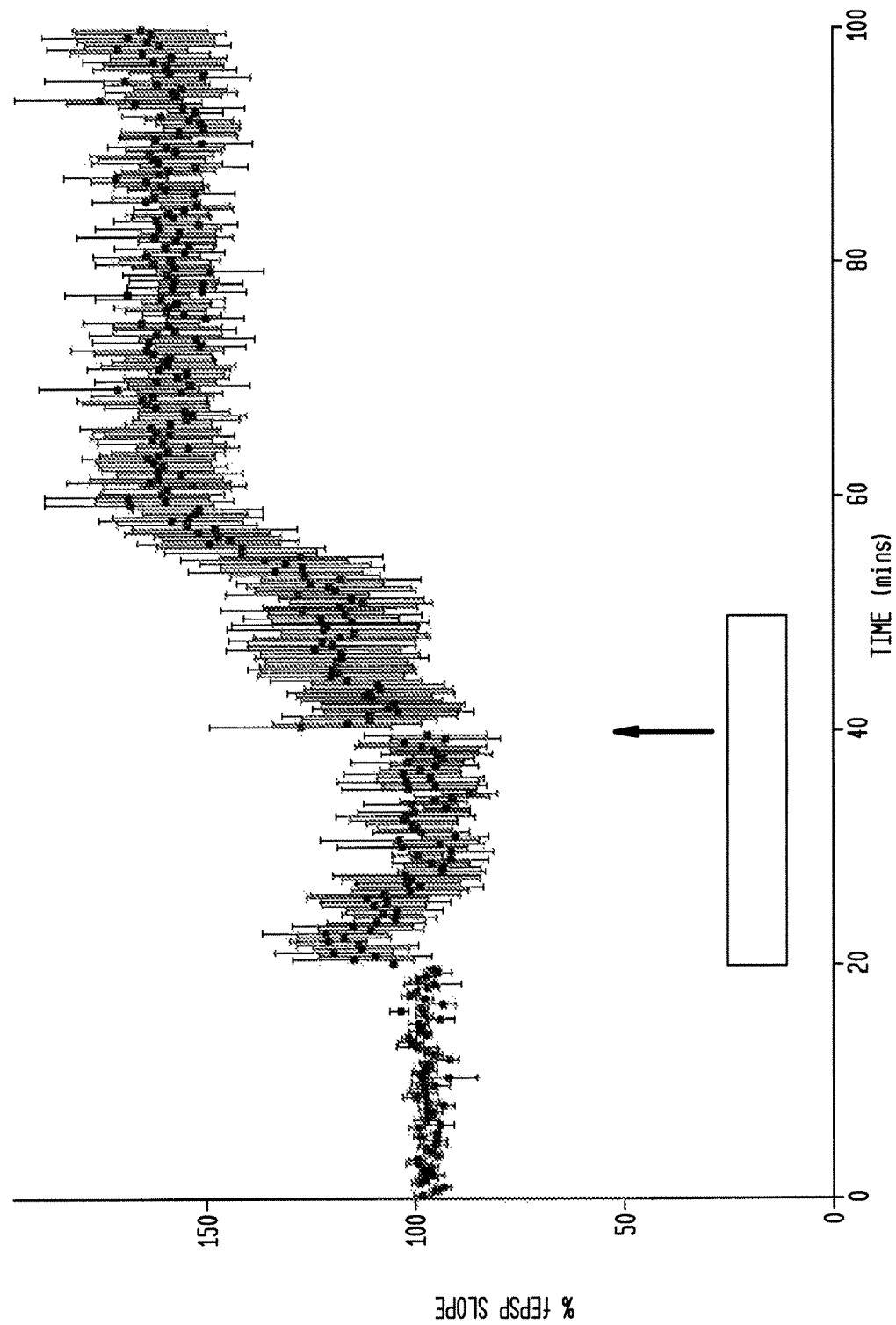
FIG. 9 displays data from AS mouse (Ube3am−/p+) hippocampal slices which were recorded for 0-20 minutes observing a stable baseline. Then CN2097 2 µM was superfused from 20-50 minutes. The arrow at 40 minutes indicates three trains of High Frequency Stimuli 10 seconds apart. The HFS is 100 pulses in 1 second with an interpulse interval of 10 ms, i.e. 100 Hz. This results in a significant increase in the synaptic strength (LTP). In AS mice this stimulation is normally unable to induce LTP (FIG. 8.). At 90-100 minutes the averaged response was 159.8+/−1.1%, n=7.

CN 2097 is effective in synaptic plasticity and is able to lower the threshold for LTP induction, as shown FIG. 2. FIG. 2 shows Sub-threshold LTP induction at the Schaffer Collateral-CA1 synapse is rescued by CN 2097. In FIG. 2, using a low intensity 1 second 100 Hz (HFS) stimulation train that normally fails to induce LTP (white circles), was added 2 μM CN 2097 which induced a significant LTP (black circles) that lasted for over 60 minutes. Without being bound by any particular theory, it is believed that CN 2097 acts through its ability to specifically interfere with NR2B activity and expression to change the sliding threshold for synaptic plasticity, altering the ratio of NR2A:NR2B. Similarly, antagonism of NR2B has been reported to lower the threshold for synaptic plasticity, such that LTP can be induced in response to a normally impotent stimulation with NMDA agonist. CN 2097 is believed to mimic this effect without displaying the toxicity and side effects associated with simple receptor antagonists that block basal transmission, since it does not act as an antagonist of the NMDA receptor (FIG. 3) nor the AMPA receptors which underlie the fEPSP (FIGS. 6(WT) and 9(AS). FIG. 3 presents a recording in the CA1 region of the hippocampus: EPSCs from a visually identified neuron in hippocampal slices before/after application of CN2097. Under whole cell configuration, NMDA-mediated component of the EPSC was isolated in the presence of NBQX (5 µM) and picrotoxin (50 µM). At the end of the experiment, APV (50 µM) was added to confirm the NMDA current component, which abolished the EPSC. The cell voltage was clamped at +40 mV and synaptic responses were recorded.

Example 1

Therapeutic Protocol

A 48 year old female presents with Angelman syndrome. Structure 1 composition is administered at 5 mg/Kg orally. The patient exhibits learning of new things that previously she was unable to acquire. Within weeks she is learning words and starts to communicate. As long as the medication is prescribed she is able to continue to learn new things. Chronic treatment with CN 2097 is instituted. The patient maintains the ability to learn new skills and does not exhibit anterograde amnesia.

Example 2

Therapeutic Protocol

A new born human infant is identified as having Angelman syndrome as tested by pre-natal genetic screening. Structure 1 composition is administered at 5 mg/Kg subcutaneously. The infant is able to develop normally, and the symptoms of AS do not become manifest. In particular, neuronal circuitry is properly developed, preventing the abnormal firing patterns normally seen in AS that result in a high prevalence of epileptic seizures. Additionally, the infant benefits from acquiring experience induced memories at the critical stages for language and motor development.

Example 2

Therapeutic Retina Protocol

The neuroprotective effects of CN2097 post-treatment against NMDA-induced ganglion cell death in the rat retina was observed. Rat eyes were given an intravitreal injection containing 20 nmol of NMDA with 3 nmol CN2097 being co-administered or injected following NMDA insult at 1, 2 or 6 hrs. Retinal ganglion cell survival was assessed by counting fluorogold-labeled cells In an defined area (between 2 and 3 mm) from the center of the optic nerve head of each retina and compared with untreated (control) retinas.

This study showed CN2097 attenuation of the signaling of NMDA-induced neuronal cell death in vivo. Matched paired retinas in the presence of CN2097 (indicated in nmol) or absence (zero) displayed a dose dependent attenuation of NMDA-induced poly(ADP-ribosyl)ation-immunoreactivity (PAR-IR) CN2097 blocked NMDA-induced loss of plasma membrane selectivity (LPMS; necrosis) as compared with a time matched NMDA-treated retina. Similarly, CN2097 also blocked NMDA-induced TUNEL-labeling in the retina. Tests included 20 nmol NMDA vs 1.2 nmol CN2097/20 nmol NMDA. CN2097 provided protection against NMDA-induced ganglion cell loss in the retina using fluorogold retrograde labeling of surviving ganglion cells viewed 14 days post insult. Data suggest that the regional distribution treated retinas are regionally identical to the distributions in the untreated retina, and are significantly protected as compared with retinas treated with NMDA-alone or those treated with the non-specific cyclic peptide CN3200/NMDA.

Example 3

Therapeutic Retina Protocol

A 50 year old male subject presents with post-stroke inflammation of both retinas. Structure 1 composition is administered at 2 mg/Kg i.v within 3 hours post-stroke. The subject exhibits a subsidence in the inflammation and the retinal cells are protected leading to no loss in visual acuity.

NO signaling is examined using guanosine 3',5'-monophosphate (cGMP) formation as a surrogate measure of NO production by Ca2+-activated nNOS56. As p38 is an important downstream effector, and disruption of NR2B/PSD-95 interactions uncouples the NMDAR from p38 activation, we will determine if CN2097 interferes with NMDA stimulation of p38 activation as measured by immunoblotting with an anti-phospho-p38 antibody. Similarly, we have investigated the effects of CN2097 on up-regulating CaMKII, p42/44 MAPK, PI3K-Akt, activation of cAMP response element-binding protein (CREB)-phosphorylation, key mediators of synaptic NMDAR-dependent signaling. To distinguish whether CN2097 acts solely on NR2B to promote signaling, neurons will be pre-exposed to the NR2B-specific antagonist Ro 25-6981 or the NR2A-specific antagonist NVP-AAM077.

Example 4

Chronic Therapeutic Protocol

A 2 year old female presents with AS was identified by clinical presentation. Structure 1 composition is administered at 8 mg/Kg/day orally. Within 6 months, diagnosed AS cognitive defects are significantly reduced and 10 years later with continued medication the subject is normal.

It is noted that the human plasma half-life of CN2097 is about 48 minutes, with particular reference to 48.2 minutes. Post i.v. CN2097 uptake into the brain has also been noted with particular reference to the hippocampus, the cerebellum and the periventricular nucleus of the hypothalmus. In addition uptake into the deep cerebellar nuclei, in the sub-cortex and the retina are noted.

The pharmacologically active compositions of this invention can be processed in accordance with conventional methods of Galenic pharmacy to produce medicinal agents for administration to patients, e.g., mammals including humans. Dosages from about 1 mg to about 10 mg per kilogram are noted with reference to about 4 to about 6 mg/Kg and particularly about 5 mg/Kg. As measured by blood levels a level of about 0.1 to about 10 µM is noted. Particular reference is made to a therapeutic concentration range of about 1 µM to about 4 µM, and more particularly at about 2 µM.

The compositions of this invention can be employed in admixture with conventional excipients, i.e., pharmaceutically acceptable organic or inorganic carrier substances suitable for parenteral, or enteral (e.g., oral or inhalation) use which do not deleteriously react with the active compositions. Suitable pharmaceutically acceptable carriers include but are not limited to water and salt solutions, e.g., saline. The pharmaceutical preparations can be sterilized and if desired mixed with auxiliary agents, e.g., salts for influencing osmotic pressure, buffers and the like which do not deleteriously react with the active compositions. They can also be combined where desired with other active agents, e.g., TPA (Tissue Plasminogen activator).

In some embodiments of the present invention, dosage forms include instructions for the use of such compositions.

For parenteral application, particularly suitable are injectable, sterile solutions, preferably oily or aqueous solutions, as well as suspensions, emulsions, or implants, including suppositories. Ampules are convenient unit dosages.

Sustained or directed release compositions can be formulated, e.g., liposomes or those wherein the active component is protected with differentially degradable coatings, e.g., by microencapsulation, multiple coatings, etc. It is also possible to freeze-dry the new compositions and use the lyophilizates obtained, for example, for the preparation of products for injection.

Generally, the compositions of this invention are dispensed in unit dosage form comprising about 1 to about 500 mg in a pharmaceutically acceptable carrier per unit dosage.

The dosage of the compositions according to this invention generally are 1 to 100 mg/kg/day, preferably 1 to 10 (especially if the general dosage range spans an order of magnitude or more), when administered to patients, e.g., humans to treat (e.g., cardiac insufficiency) analogously to the known agent (hydrochlorothiazide (HydroDIURIL®), and is to 25-50 mg daily TID mg/kg/day when administered to treat (hypertension); (repeat for all activities and indications). Alternatively, treat as an IV bolus, then IV infusion similar to Thrombolytic agents such as alteplase (TPA). or antiarrhythmic drugs e,g, atenolol (IV 50 10 mg) or anti-Parkinson drugs benztropine (Congentin®) IV 1-6 mg daily, or entacapone 200-1,600 mg.

It will be appreciated that the actual preferred amounts of active compositions in a specific case will vary according to the specific compositions being utilized, the particular compositions formulated, the mode of application, and the particular situs and organism being treated. Dosages for a given host can be determined using conventional considerations, e.g., by customary comparison of the differential activities of the subject compositions and of a known agent, e.g., by means of an appropriate, conventional pharmacological protocol.

We claim:

1. Inducing long-term potentiation in a subject by the method of administering a therapeutically effective dose of the compound CN2097.

2. The method of claim 1 wherein said dosage is from about 1 mg/Kg to about 10 mg/Kg.

3. The method of claim 2 wherein said dosages are from about 4 mg/Kg to about 6 mg/Kg.

4. The method of claim 3 wherein said dosage is about 5 mg/Kg.

5. The method of claim 1 wherein said dosage establishes a blood level of about 0.1 to about 10 µM.

6. The method of claim 5 wherein said blood level is from about from about 2 µM to about 4 µM.

* * * * *

UNITED STATES PATENT AND TRADEMARK OFFICE
CERTIFICATE OF CORRECTION

| | | |
|---|---|---|
| PATENT NO. | : 8,673,857 B2 | Page 1 of 1 |
| APPLICATION NO. | : 13/389047 | |
| DATED | : March 18, 2014 | |
| INVENTOR(S) | : John Marshall et al. | |

It is certified that error appears in the above-identified patent and that said Letters Patent is hereby corrected as shown below:

In the Claims

Column 14, line 30, delete "from about", second occurrence.

Signed and Sealed this
Sixteenth Day of September, 2014

Michelle K. Lee
*Deputy Director of the United States Patent and Trademark Office*